US00PP26842P3

(12) United States Plant Patent
Verhoef

(10) Patent No.: US PP26,842 P3
(45) Date of Patent: Jun. 21, 2016

(54) ***WEIGELA* PLANT NAMED 'VELDA'**

(50) Latin Name: *Weigela florida*
Varietal Denomination: Velda

(71) Applicant: Gijsbertus Verhoef, Hazerswoude (NL)

(72) Inventor: Gijsbertus Verhoef, Hazerswoude (NL)

( * ) Notice: Subject to any disclaimer, the term of this patent is extended or adjusted under 35 U.S.C. 154(b) by 204 days.

(21) Appl. No.: 13/999,609

(22) Filed: Mar. 12, 2014

(65) Prior Publication Data

US 2015/0264852 P1 Sep. 17, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO: Plant Variety Database, Nov. 21, 2015, citation for 'Velda'.*

* cited by examiner

*Primary Examiner* — Susan McCormick Ewoldt
*Assistant Examiner* — Karen Redden

(57) ABSTRACT

A new cultivar of *Weigela* plant named 'Velda' that is characterized by a compact habit, white funnelform shaped flowers and purple-black colored foliage.

1 Drawing Sheet

Botanical classification: *Weigela florida.*
Variety denomination: 'Velda'.

BACKGROUND OF THE INVENTION

The present invention relates to a new and distinct cultivar of *Weigela* plant botanically known as *Weigela florida* and hereinafter referred to by the cultivar name 'Velda'.

The new cultivar is the product of a breeding program conducted by the inventor in a cultivated area of Hazerswoude, The Netherlands. The objective of the breeding program was to develop new *Weigela* cultivars with dark foliage and white flowers.

'Velda' originated from the crossing of the female or seed parent *Weigela florida* 'Milk and Honey' (not patented) and the male or pollen parent, *Weigela florida* 'Alexandra' (U.S. Plant Pat. No. 10,772) in 2008. The cultivar 'Velda' was selected by the inventor in 2010 as a single plant within the progeny of the stated cross in a cultivated area of Hazerswoude, The Netherlands.

Asexual reproduction by softwood cuttings of the new cultivar 'Velda' was first performed in 2010 in Hazerswoude, The Netherlands. Since that time, under careful observation, the unique characteristics of the new *Weigela* cultivar have been uniform, stable and reproduced true to type in successive generations of asexual reproduction.

SUMMARY OF THE INVENTION

The following represent the distinguishing characteristics of the new *Weigela* cultivar 'Velda'. These traits in combination distinguish 'Velda' as a new and distinct cultivar apart from all other existing varieties of *Weigela* known to the inventor. 'Velda' has not been tested under all possible conditions and phenotypic differences may be observed with variations in environmental, climatic, and cultural conditions, however, without any variance in genotype.

1. *Weigela* 'Velda' exhibits a compact habit.
2. *Weigela* 'Velda' exhibits abundant white funnelform shaped flowers.
3. *Weigela* 'Velda' exhibits purple-black colored foliage.

The closest comparison plant is *Weigela* 'Bristol Snowflake' (not patented). The new cultivar 'Velda' is distinguishable from 'Bristol Snowflake' in having a shorter overall height and purple-black leaves. In contrast, the leaves of 'Bristol Snowflake' are green.

The new cultivar 'Velda' is distinguishable from the female parent 'Milk and Honey' in having a shorter overall height and purple-black leaves. In contrast, the leaves of 'Milk and Honey' are green.

The new cultivar 'Velda' is distinguishable from the male parent *Weigela* 'Alexandra' in having a shorter overall height and white flowers. In contrast, the flowers of 'Alexandra' are purple-red.

BRIEF DESCRIPTION OF THE DRAWING

The accompanying photograph illustrates the distinguishing traits of *Weigela* 'Velda'. The plant in the photograph shows an overall view of a 2 year old plant grown outdoors in a 5 liter container.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Weigela* cultivar named 'Velda'. Data was collected in Hazerswoude, The Netherlands from 2 year old plants grown outdoors in 5 liter containers. The time of year was Summer and the temperatures ranged from 12-25° Centigrade during the day, and 4-15° Centigrade during the night. The light level was natural outdoor light and there were no photoperiodic treatments or growth retardants used. Color determinations are in accordance with The Royal Horticultural Society Colour Chart, 5th edition 2007, except where general color terms of ordinary dictionary significance are used. The growing requirements are similar to the species.

Botanical classification: *Weigela florida* 'Velda'.

Parentage: 'Velda' resulted from the crossing of the female or seed parent *Weigela* 'Milk and Honey' and the male or pollen parent, *Weigela* 'Alexandra'.

Annual or perennial: Perennial.

Plant type: Shrub.

Suitable container size: 1.5 liter and larger.

Plant shape: Broad ovate shaped.

Growth habit: Broad upright.

Height: Average 30.2 cm. in height.

Width: Average 35.1 cm. in diameter.

Vigor: Moderate.

Growth rate: In spring approximately 8 cm. per month.

Low temperature tolerance: USDA Zone 5.

High temperature tolerance: At least 35 degrees Centigrade.

Propagation: Softwood cuttings.

Time to initiate roots: 21 to 28 days are required to initiate roots at 18 degrees Centigrade in the summer.

Time to produce a rooted plant: 60 days are required to produce a rooted plant at 16-22 degrees Centigrade in the summer.

Crop time: Approximately 18 months are required to achieve a finished plant from cuttings.

Root system: Main roots moderately thick, other roots moderately fine.

Stem:

*Branching habit*.—Free branching.

*Basal branching*.—Yes.

*Average number of lateral branches*.—4 main branches with 8 lateral branches per main branch.

*Pinching*.—Not required, pinching will improve branching.

*Lateral branch diameter*.—Average 3 mm. in diameter.

*Lateral branch length*.—Average 15.6 cm. in length.

*Internode length*.—Approximately 3.2 cm. between nodes.

*Stem appearance*.—Slightly quadrangular in shape, moderately glossy, older branches rounded.

*Stem aspect*.—Upright to outward with an average angle 40 degrees from vertical.

*Stem strength*.—Moderate.

*Stem color immature*.—144A with upper side tinged N199A.

*Stem color mature*.—Varies from 197C to 199D.

*Pubescence*.—Young shoots covered with soft short hairs, average 0.5 mm. in length, 155A in color.

Foliage:

*Leaf arrangement*.—Opposite.

*Compound or single*.—Single.

*Quantity of leaves per lateral branch*.—Average 10.

*Leaf shape*.—Elliptic to ovate.

*Leaf tip*.—Short apiculate.

*Leaf base*.—Short attenuate.

*Leaf margin*.—Finely serrate.

*Leaf dimensions*.—Length: 6.6 cm, width: 3.7 cm.

*Leaf texture* (*both sides*).—Slightly glossy.

*Pubescence*.—Main vein on upper side and main and secondary veins on lower side moderately covered with soft short hairs, 0.4 mm. in length, color 156D.

*Vein pattern*.—Pinnate.

*Leaf color young, upper surface*.—In between 200A and 202A.

*Leaf color young, lower surface*.—200C.

*Leaf color mature, upper surface*.—N137A, heavily tinged 200A.

*Leaf color mature, lower surface*.—147B with tinges of N200A and N200B.

*Vein color, upper side*.—144B.

*Vein color, under side*.—144B.

*Leaf attachment*.—Petiolate.

*Petiole dimensions*.—0.6 cm. in length, 0.2 cm. in width and 0.15 cm. in height.

*Petiole color*.—144B with tinges of 200B.

*Durability of foliage to stress*.—High.

Flower:

*Flower arrangement*.—Terminal thryse.

*Inflorescence type*.—Thryse.

*Inflorescence dimensions*.—5.6 cm. in height and 8.0 cm. in width.

*Quantity of flowers per inflorescence*.—Average 7.

*Flower type*.—Single, funnelform.

*Flowering habit*.—Continuous throughout summer.

*Natural flowering season*.—Spring to early autumn.

*Time to flower from planting*.—Approximately 7 months.

*Quantity of flower buds per lateral stem*.—Average 3.

*Quantity of flowers per lateral stem*.—Average 4.

*Quantity of flowers and buds per plant*.—Average 225.

*Rate of flower opening*.—Approximately 75% of flowers are open at once.

*Fragrance*.—None.

*Bud length*.—Average 2.3 cm.

*Bud diameter*.—Average 0.8 cm. in diameter.

*Bud shape*.—Narrow obovate.

*Rate of opening*.—Approximately 5 days.

*Bud color*.—145B with base 174C to 174D.

*Flower aspect*.—Outward to slightly drooping.

*Flower shape*.—Funnelform.

*Flower dimensions*.—Average 2.6 cm. in diameter and 3.9 cm. in height.

*Flower longevity*.—Approximately 12 days.

*Persistent or self-cleaning*.—Self-cleaning.

*Number of petals*.—Five in number.

*Petal arrangement*.—Rotate, fused into a funnelform shaped corolla.

*Petal appearance*.—Matte, velvety.

*Petal texture*.—Smooth (both sides).

*Petals fused*.—Yes, lower 72.5% fused.

*Petal shape*.—Spathulate.

*Petal margin*.—Entire.

*Petal apex*.—Obtuse.

*Petal dimensions*.—Average 3.5 cm. in length and free part 1.1 cm. in width.

*Petal color when opening* (*upper side*).—150D, base 176A with mark 5A.

*Petal color when opening* (*under side*).—150D, base tinged 174D.

*Petal color fully opened* (*upper side*).—Varies from 155A to 157D, base 180D with marks 15B and 47C.

*Petal color fully opened* (*under side*).—155A, base 161A.

*Petal color fading to*.—Not fading.

Sepals:

*Number of sepals*.—Average 5.

*Sepal arrangement*.—Rotate.

*Sepal texture* (*both surfaces*).—Covered with short hairs, length 0.5 mm, color 156D.
*Sepal shape*.—Linear.
*Sepal margin*.—Entire.
*Sepal apex*.—Narrow acute.
*Sepal base*.—Narrow cuneate.
*Sepal dimensions*.—Average 8 mm. in length and 0.1 mm. in width.
*Sepal color, young* (*upper side*).—146A and 176A.
*Sepal color, young* (*under side*).—176A and 200A.
*Sepal color, mature* (*upper side*).—146A and 176A.
*Sepal color, mature* (*under side*).—176A and 200A.

Calyx:
*Calyx shape*.—Rotate.
*Calyx dimensions*.—Average 8 mm. in length and 6 mm. in diameter.

Peduncle:
*Peduncle dimensions*.—Average 1.8 cm. in length and 0.15 cm. in diameter.
*Peduncle angle*.—0° from lateral branch.
*Peduncle strength*.—Strong.
*Peduncle color*.—146B, upper side tinged 200A.

Pedicels:
*Pedicel dimensions*.—Average 15 mm. in length and 1 mm. in diameter.
*Pedicel angle*.—20° from peduncle.
*Pedicel strength*.—Strong.
*Pedicel color*.—200A.

Reproductive organs:
*Stamen number*.—Average 5.
*Anther shape*.—Dorsifixed, narrow oblong, filaments implanted on corolla.
*Anther length*.—4 mm.
*Anther color*.—159C.
*Filament length*.—8 mm.
*Filament color*.—N155B.
*Amount of pollen*.—Low.
*Pollen color*.—158D.
*Number of pistils*.—Average 1.
*Pistil length*.—3.4 cm.
*Stigma shape*.—Club shaped.
*Stigma color*.—157D.
*Style length*.—3.2 cm.
*Style color*.—N155B, base N170D.
*Ovary color*.—200B.
*Ovary pubescence*.—Sparsely covered with very short hairs, 0.05 cm. in length, color 155A.

Fruit and seed production: Fruit and seed development has not been observed to date.

Disease and pest resistance: Disease and pest resistance has not been observed to date.

The invention claimed is:

1. A new and distinct variety of *Weigela* plant named 'Velda' as described and illustrated.

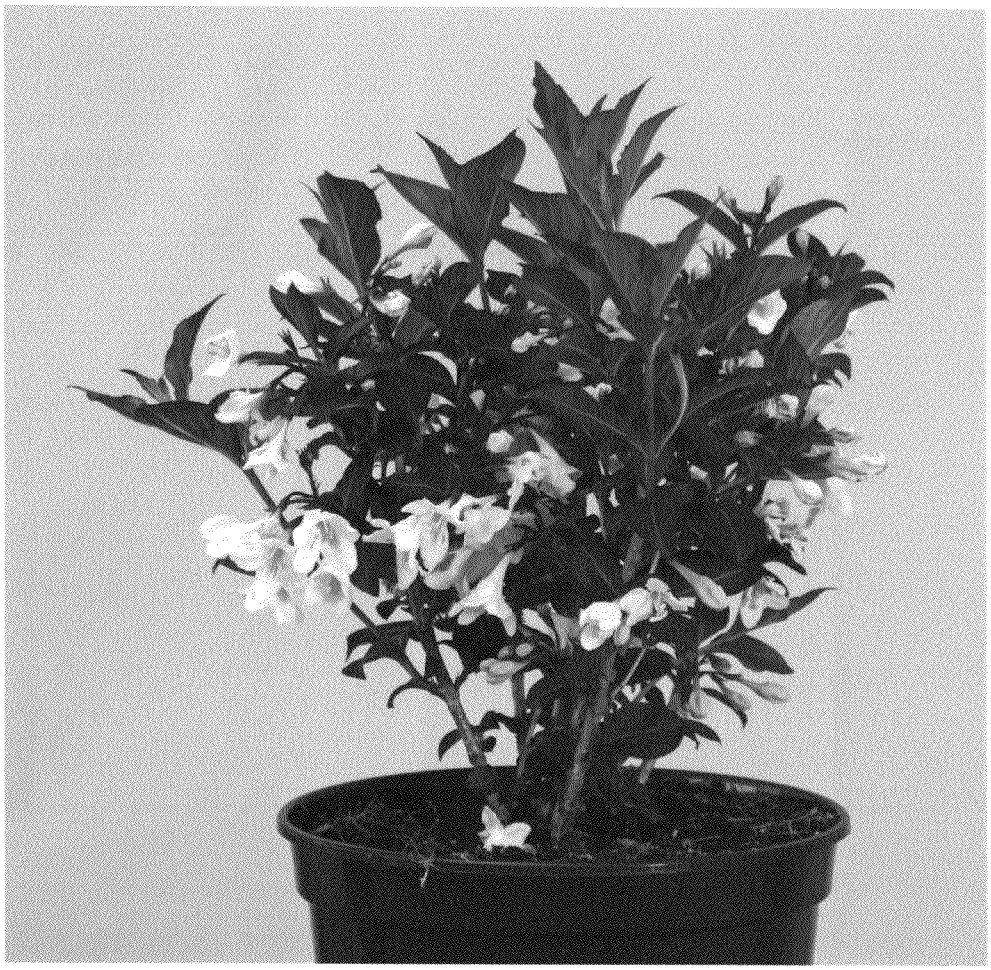

* * * * *